United States Patent [19]

Ornstein

[11] 4,367,742

[45] Jan. 11, 1983

[54] OSTOMY BAG

[76] Inventor: Murray Ornstein, 115 Fairfield Dr., Short Hills, N.J. 07480

[21] Appl. No.: 192,124

[22] Filed: Sep. 29, 1980

Related U.S. Application Data

[63] Continuation-in-part of Ser. No. 43,170, May 29, 1979, abandoned.

[51] Int. Cl.³ .............................................. A61F 5/44
[52] U.S. Cl. ............................ 128/283; 128/DIG. 24
[58] Field of Search ................... 128/283, 272, 272.1, 128/272.3, 275, DIG. 24, 214 D

[56] References Cited

U.S. PATENT DOCUMENTS

| | | | |
|---|---|---|---|
| 3,055,368 | 9/1962 | Baxter | 128/283 |
| 3,618,606 | 11/1971 | Brown et al. | 128/283 |
| 3,690,320 | 9/1972 | Riely | 128/283 |
| 3,837,342 | 9/1974 | Mitsuo | 128/283 |
| 4,185,630 | 1/1980 | Neumeier et al. | 128/283 |

FOREIGN PATENT DOCUMENTS

| | | | |
|---|---|---|---|
| 2620129 | 11/1976 | Fed. Rep. of Germany | 128/283 |
| 1719063 | 11/1954 | United Kingdom | 128/283 |

Primary Examiner—Richard J. Apley
Assistant Examiner—T. J. Wallen
Attorney, Agent, or Firm—Melvin K. Silverman

[57] ABSTRACT

The present invention discloses an improvement in an ostomy bag which permits undesirable gases to escape only after passing through a separate deodorant filled chamber. The chamber is located at the top of the bag and an interconnecting tube provides for the passage of the gases from the bag to the deodorant chamber. A similar tube connected to the deodorant chamber allows the deodorized gases to pass into the atmosphere. A single use or renewable use design is disclosed.

7 Claims, 6 Drawing Figures

U.S. Patent    Jan. 11, 1983    4,367,742
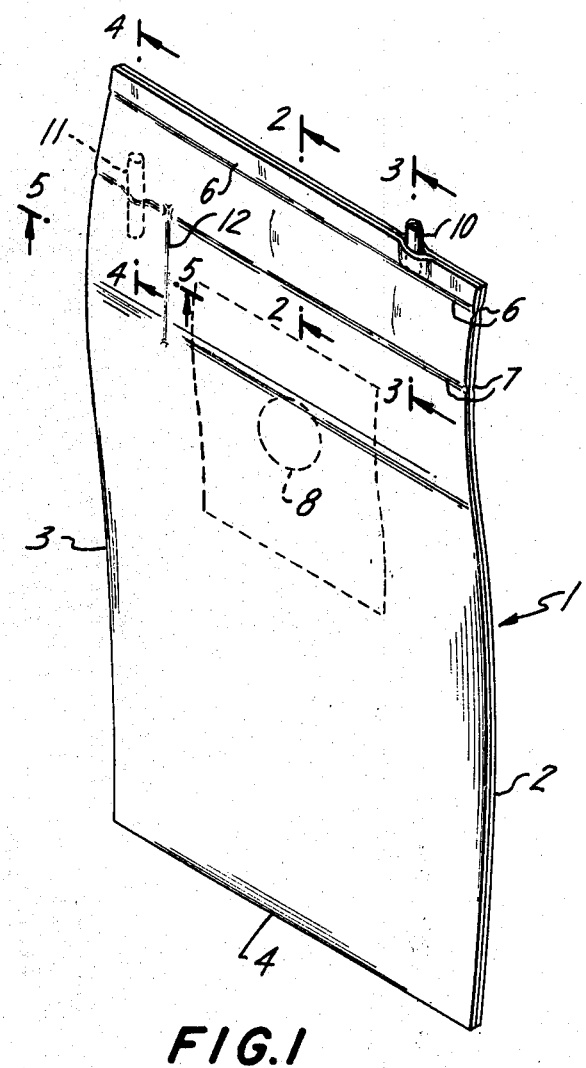
FIG.1
FIG.4
FIG.5
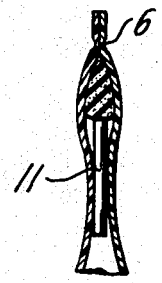
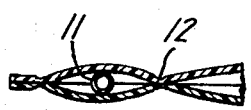
FIG.6
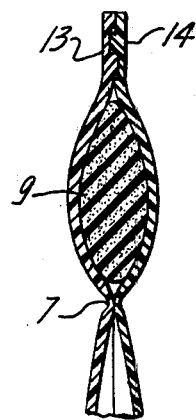

OSTOMY BAG

CROSS REFERENCE

This is a continuation-in-part application of application Ser. No. 043,170 filed May 29, 1979, now abandoned.

BACKGROUND OF THE INVENTION AND PRIOR ART

The present invention relates to an improved ostomy bag to be worn by a person having a stoma formed in a colostomy, ileostomy, urostomy or the like. Such surgical procedures often involve the diversion of the intestines or other parts of the human body through the person's abdominal wall to form a stoma which permits the discharge and drainage from the human body of waste products such as fecal matter or urine. This drainage through the stoma is with little or no control by the person having the operation and it is necessary to provide a container such as an ostomy bag affixed to the body to cover the stoma and to collect these waste products.

There are numerous United States patents dealing with various designs of ostomy bags. However, only two are known that include means to deodorize gases. These are Riely U.S. Pat. No. 3,690,320 (1972) and German Pat. No. 2,620,129 (1976). Riely provides a deodorizing packet within the interior of an ostomy bag, with the packet having a rupturable seal. When deodorization is needed, the wearer of the bag exerts mild pressure against the packet to rupture the seal, thereby deodorizing the contents of the bag. German Pat. No. 2,620,129 discloses a foam like material containing deodorant located in a sealed chamber at the top of the ostomy bag. The chamber wall intermediate the bag and the chamber is perforated so that when the wearer prepares the bag for use, he can remove the seal over the perforated wall and thereby allow deodorant to pass into the ostomy bag. U.S. Pat. No. 3,055,368 is also of interest since it provides for the venting of gases contained in an ostomy bag.

The present invention moves beyond the above-mentioned prior art in that it provides a simple, economical and effective method of deodorizing gases and at the same time provides for the continuous escape of the gases into the atmosphere.

SUMMARY OF THE INVENTION

The present invention comprises an improvement in an ostomy bag of the type fabricated substantially of thin plastic sheets and having a stoma opening on one side of the bag. The improvement comprises introduction of a chamber at the top of the ostomy bag and openings between the bag and the chamber and the atmosphere. The chamber contains cloth or other open cellular-like means for holding the deodorant. The chamber can be constructed for a single use or renewable uses.

It is an object of this invention to provide an improved ostomy bag which automatically releases deodorized gases originating in the bag and into the atmosphere, thereby avoiding any specific effort by the wearer of the bag to deodorize and vent malodorous gases.

It is another object to provide a simple, effective and economical ostomy bag that simultaneously deodorizes and vents and is renewable for multiple uses.

It is also an object of the invention to provide an ostomy bag that is simple and economical in its construction and other objects and advantages of the invention will appear from the following description. In the description, reference is made to the accompanying drawings which form a part hereof, and which there is shown by way of illustration, and not of limitation, a specific form of the invention.

BRIEF DESCRIPTION OF THE DRAWINGS

FIG. 1 is a view in perspective of the ostomy bag of this invention.

FIG. 2 is a sectional view of a portion of the ostomy bag taken along the line 2—2 of FIG. 1.

FIG. 3 is a sectional view of a portion of the ostomy bag taken along the line 3—3 of FIG. 1.

FIG. 4 is a sectional view of a portion of the ostomy bag taken along the line 4—4 of FIG. 1.

FIG. 5 is a sectional view of a portion of the ostomy bag taken along the line 5—5 of FIG. 1.

FIG. 6 is an optional construction of the cross-section shown in FIG. 2.

DETAILED DECRIPTION OF THE INVENTION

Referring to the drawings, and more specifically to FIG. 1, a pliable impermeable bag 1 is formed from a thermally responsive material such as polyethylene. The side edges 2 and 3 are sealed for their entire length as is also bottom edge 4. Cross seals 6 and 7, with a significant space between them, extend the entire width of the bag, with the exception of a small opening or interruption at a predetermined location along its length. The stoma opening 8 is located below the seal 7 and may be of any number of constructions well known in the art.

Seals 6 and 7 and the top portions of seals 2 and 3 define a generally rectangular chamber with a typical vertical section shown in FIG. 2. Placed inside this chamber is a deodorant carrier 9 which can be any number of known materials such as cotton, woven or nonwoven cloth, gauze and open celled foams of PVC or the like.

Referring to FIG. 3, there is shown nipple 10 sealed in seam 6 providing an exit into the atmosphere for deodorized gases in the upper chamber. The untreated gases will have entered into the chamber through nipple 11 sealed in seam 7, as shown in FIG. 4. Although the use of nipples 10 and 11 are not esssential to form the openings in seams 6 and 7, it is the preferred embodiment of the invention. Additionally, for maximizing deodorizing efficiency, the openings 10 and 11 have been located at opposite ends of the chamber.

Another optional feature is partial seal 12 which intersects seal 7 and generally lies intermediate nipple 11 and stoma opening 8. Applicant has found that this seam reduces the frequency of clogging of the opening into the deodorant chamber.

The construction described above represents a single use product. The carrier 9 and deodorant can be placed at the factory and all openings temporarily seal until it is ready for use. An alternative construction for the central portion of seam 6 is shown in FIG. 6. A well-known female profile 13 and male profile 14 can be used to provide entry into the deodorant chamber to replenish the deodorant. This feature would be very desirable with reusable bottom opening bags well known in the art. Elements 13 and 14 act somewhat as a sealing zipper but other mechanical means such as clips, would also be acceptable.

The specific structure described hereinabove and in the attached drawings is illustrative only and any variations thereof apparent to one skilled in the art are contemplated to fall within the scope and spirit of the following claims.

What is claimed is:

1. An ostomy bag of the type adapted to be attached to the body of the patient and formed of two thin sheets of tough but pliable material having the general characteristics of polyethylene, welded together at the peripheral edges thereof with one sheet constituting the body-side of the bag and the other sheet the outer-side of the bag and having, further, a small intake orifice near the top of the body-side sheet, a mounting pad connected to the ostomy bag to the body of the patient, and an integrally formed escape opening for accumulated gas, the improvement comprising:

a gas permeable, re-openable and re-sealable deodorant chamber intermediate the gas escape opening and a gas entrance opening into the chamber from the ostomy bag, said bag further comprising a deodorant carrier having substantially the same volume and configuration as the inside of the said deodorant chamber and said carrier completely filling said chamber.

2. The ostomy bag of claim 1 wherein the gas escape and entrance openings are at opposite ends of the chamber.

3. The ostomy bag of claim 1 wherein the deodorant is contained by a porous means.

4. The ostomy bag of claim 3 wherein the porous means is taken from the group consisting of gauze, cotton, cloth, non-woven cloth and an open celled plastic.

5. The ostomy bag of claim 1 wherein the resealable opening comprises male and female profile in the chamber walls such that when pressed together they provide a gas-tight seal.

6. The ostomy bag of claim 1 wherein the escape and entrance openings are formed of nipples.

7. The ostomy bag of claim 1 wherein the entrance opening to the deodorant chamber is protected by a seam joining the two opposing walls of the bag, starting at the adjacent chamber seam and extending into the ostomy bag, terminating in the region of the stoma opening.

* * * * *